United States Patent [19]

Rahikainen

[11] Patent Number: 4,927,261
[45] Date of Patent: May 22, 1990

[54] METHOD AND APPARATUS FOR PHOTOGRAPHING A MOVEMENT

[76] Inventor: Ahti Rahikainen, Kääpäkuja 12, 00760 Helsinki, Finland

[21] Appl. No.: 251,898

[22] Filed: Sep. 30, 1988

[30] Foreign Application Priority Data

Oct. 6, 1987 [FI] Finland .................................. 874374

[51] Int. Cl.$^5$ ...................... G03B 19/18; G03B 21/32
[52] U.S. Cl. .......................................... 352/39; 356/25
[58] Field of Search ............................. 352/39; 356/25

[56] References Cited

U.S. PATENT DOCUMENTS

4,522,475  6/1985  Ganson .................................. 352/39

Primary Examiner—Monroe H. Hayes
Attorney, Agent, or Firm—McAulay Fisher Nissen & Goldberg

[57] ABSTRACT

Method and photographic apparatus for performing motion studies on a moving subject. The moving subject is photographed through a rotating disc having at least one transparent aperture and a plurality of filter apertures covered with filter plates. Opaque regions of the disc separate the apertures from one another. Preferably, miniature spotlights are connected to moving points of the subject that are desired to be studied. Each of the spotlights projects a beam having essentially one selected wavelength to pass through the filter apertures and the filter plates. Incident background light, lighting the subject, is prevented from passing through the filter apertures by virtue of the filter plates. As a result, a photograph produced by the camera includes a series of light-streak images produced by the motion of the spotlights and the light emitted by the spotlights entering the filter apertures. Interruptions in the light-streaks are produced by the opaque regions of the disc. Additionally, the photograph also includes a series of stroboscopic images of the subject produced by the incident background light reflecting from the subject and entering the camera through the transparent aperture.

16 Claims, 4 Drawing Sheets

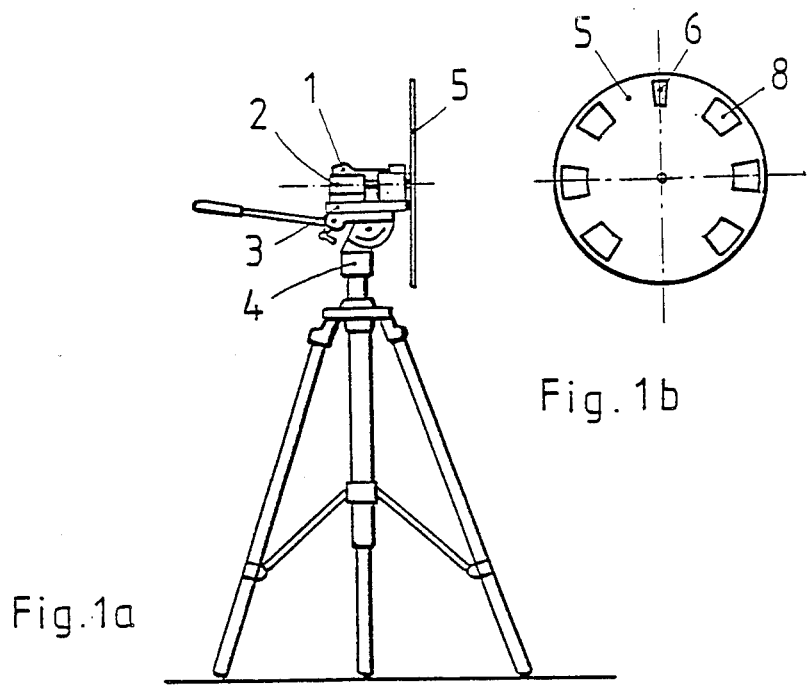
Fig. 1a
Fig. 1b
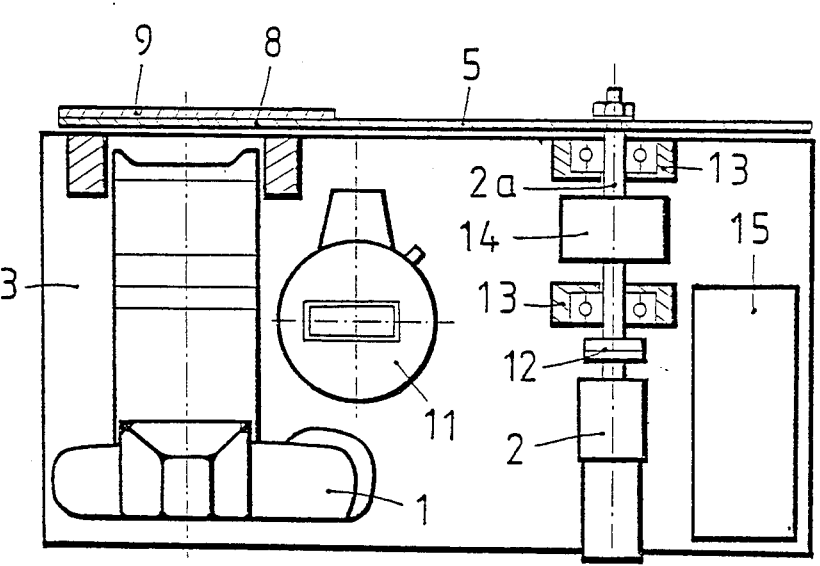
Fig. 2

METHOD AND APPARATUS FOR PHOTOGRAPHING A MOVEMENT

FIELD OF THE INVENTION

The present invention relates to a method and photographic apparatus for performing motion studies on a moving subject.

BACKGROUND OF THE INVENTION

As is well known in the art, the study of movement of a subject is often an essential component of basic research performed in many different scientific fields of endeavor. In order to obtain usable information about the motion of a moving subject, the prior art has provided various photographic techniques that may be grouped under the following headings: photography, stroboscopic photography, light-streak photography, video, fast video and camera-computer systems developed to analyse motion. An example of a prior art apparatus that is used in such photographic techniques appears in Rahikainen, A., Häkkinen, K.; Eräs liikkeen valokuvausmenetelmä ja sen hyväksikäyttö liikkumisturvallisuuden tutkimisessa. Työ ja ihminen 1(1987) 2, 104–114.

The two most common photographic techniques that are used for motion studies are light-streak photography and stroboscopic photography. In light-streak photography, miniature spotlights are attached to the moving subject at points of interest that are to be studied in detail. Each of the spotlights generates a beam of light having a selected wavelength. Background lighting is also provided for the subject. The background lighting has another selected wavelength. A filter, mounted in front of the camera allows the transmission of the light produced by the spotlights and prevents the transmission of the light produced by the background lighting reflecting from the subject and the background. A high intensity flash unit produces light that penetrates the filter to produce an image of the subject. Thus, in the photograph produced by the camera, an image of the subject is recorded together with an image of the path of the spotlights, referred to in the art as light-streaks. In stroboscopic photography, the moving subject is seen as a sequence of pictures in a single photograph. Stroboscopic photographs are produced by either lighting the subject by a flashing light of a stroboscopic lamp or by photographing the subject by a camera that has a rotating slit disc that acts as a shutter. Very similar photographs are obtained with either method of stroboscopic photography. However, the slit disc method of stroboscopic photography is more versatile than the stroboscopic lamp method in that photographs may be produced both in sunlight as well as with artificial light. In stroboscopic photography that utilizes a stroboscopic lamp, photographs may only be produced in a darkened environment so that the subject is illuminated by only the flashing stroboscopic lamp.

Light-streak photography and stroboscopic photography produce different kinds of information about the movement of the subject. Light-streak photography marks the path of movement of a moving point of the subject with a miniature spotlight and stroboscopic photography illustrates different phases of the movement as a sequence of pictures. In more specific terms, the light-streaks produced by the spotlights enable one to obtain the path and the velocity of a particular moving point of interest. The sequence of pictures obtained by stroboscopic photography enables one to identify the movements. As can be appreciated, if these two photographic methods were combined, more information would be available, concerning the movement of the subject, than could be obtained by either of the methods standing alone.

The present invention proposes to accomplish the aforesaid by providing an apparatus for producing a photograph containing a stroboscopic sequence of images of the subject together with a series of light-streak images produced by miniature spotlights attached to the subject at the specific moving points of interest. Since both images appear in a single photograph, the different phases of the movement of the subject may be correlated with the light-streaks. This is accomplished in the present invention by an apparatus that includes a rotating disc having a set of filtered apertures and one or more transparent apertures. The filtered apertures are separated from one another and from the transparent apertures by opaque regions of the disc. As the disc rotates in front of a camera and the subject moves between a reflective, darkened backdrop and the apparatus, the light produced by miniature spotlights, attached to the subject, passes through the filter apertures to form light-streak images on a photograph produced by the camera. Background lighting is provided that reflects off the subject and passes through the transparent apertures to produce stroboscopic images of the subject that illustrate the different phases of the motion of the subject.

The advantages of the present invention are manifest. The central advantage of the present invention is that the method and apparatus produces a photograph illustrating a general picture of the motion of the subject. Moreover, different phases and paths of the movement, contained in the motion of the subject, are obtained in a form in which the mathematical and physical nature of the motion may be perceived. Since the light streak and stroboscopic effects are combined and may be viewed in the single photograph, a new and completely different representation of the motion of the subject is obtained over conventional photographic methods.

A further advantage is that the photographic apparatus of the present invention can be used in both natural lighting and in artificial lighting without modification of the apparatus. In this regard, as will become apparent, the apparatus of the present invention may also be inexpensively and simply constructed.

As an ancillary feature of the invention, as will also become apparent, the apparatus and method of the present invention may be easily modified for different applications by appropriate selection of the spotlights, the filters, the reflectivity of the backdrop and the width and spacing of the apertures.

DISCLOSURE OF THE INVENTION

The present invention provides a method and apparatus for photographing a moving subject in order to study the motion of the subject. A background lighting source is provided to externally illuminate the subject. The background lighting source may either be natural or artificial. Also provided are means, connected to at least one moving point of the subject, for generating at least one light beam of essentially one selected wave length. A darkened backdrop is provided, behind the subject, to enhance the visibility of the at least one light beam. The apparatus of the present invention includes a camera for photographing the subject, means for mounting the camera in front of the subject, a rotating disc, and means for rotating the disc in front of the camera.

The disc has at least one transparent aperture allowing transmission of the light of the background lighting source reflected from the subject. The disc also has a plurality of filter apertures circumferentially spaced from one another and from the at least one transparent aperture. A plurality of opaque regions of the disc separate the filter apertures from one another and the at least one transparent aperture from the filter apertures. Means, connected to the disc and associated with the filter apertures, filter light such that only the light of the essentially one selected wave length is transmitted through the filter apertures.

The rotation means rotate the disc in front of the camera such that the at least one light beam and the reflected light enter the camera through, respectively, the filter and transparent apertures. As a result, a photograph produced by the camera comprises a series of light-streaks, a series of interruptions between the light streaks and a series of stroboscopic images. The light-streaks are produced by the at least one light beam entering the camera through the filter apertures. The interruptions are produced by the opaque regions between the filter apertures. Lastly, the series of stroboscobic images of the subject are produced by the reflected light entering the camera through the at least one transparent aperture. Each stroboscopic image is produced each time the at least one transparent aperture passes in front of the camera.

In accordance with the present invention, the filter apertures can comprise a pair of sets of three apertures located on either side of the at least one transparent aperture. Additionally, the disc can have a pair of transparent apertures located between the sets of filter apertures. In such an embodiment, the disc may be formed so that the opaque regions separating the filter apertures are narrow as compared with the width of the filter apertures to produce long light-streaks and short interruptions between the long light-streaks.

BRIEF DESCRIPTIONS OF THE DRAWINGS

In the accompanying drawings:

FIG. 1a is a side view of a photographic apparatus used in carrying out the method of the present invention.

FIG. 1b is a front elevational view of a rotating disc according to the present invention that may be used in the apparatus illustrated in FIG. 1a.

FIG. 2 is a top plan view of the photographic apparatus.

DESCRIPTION OF THE INVENTION

Figure 3:
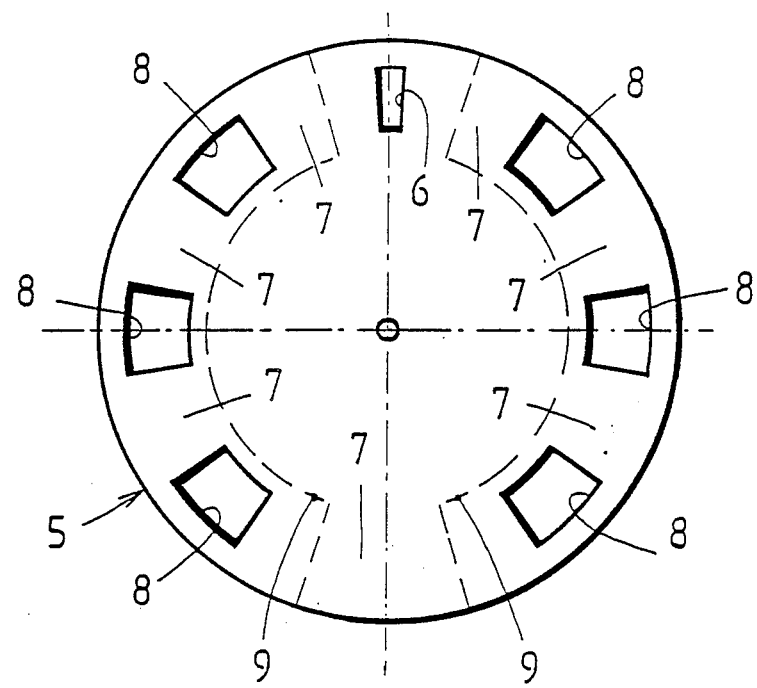
FIG. 3 illustrates one modification of a rotating disc according to the present invention having narrow apertures to produce short interrupted light-streaks and short intervals between the light-streaks.

With reference to FIGS. 1 and 2, the photographic apparatus of the present invention consists of a stable platform that may be selectively positioned in front of a darkened, reflective backdrop. The platform preferably comprises tripod 4 on which baseplate 3 is mounted. Camera 1 for producing a photographic exposure is mounted on baseplate 3 together with a rotation motor 2 and a tachometer 11. A rotating, apertured disc is fastened to a shaft 2a, and shaft 2a is attached to baseplate 3 by means of a set of bearings 13. Coupling 12 connects to motor 2. A Flywheel 14 is attached to shaft 2a between the bearings 13. As illustrated, camera 1 is positioned on the plate 3 so that the apertures of the disc 5 pass in front of the camera. For this purpose, as shown here, disc 5 and camera 1 are orthogonally related.

Figure 4:
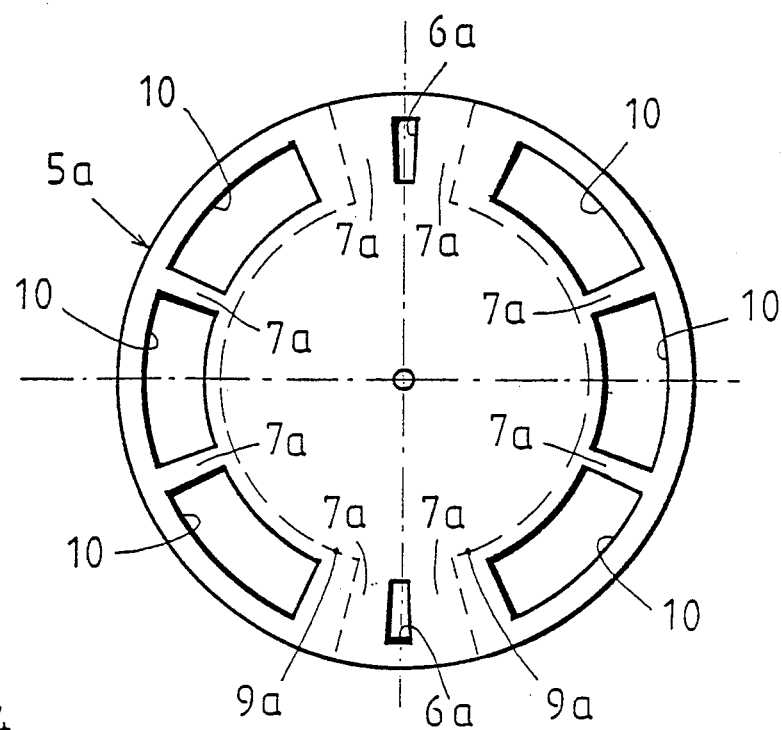
FIG. 4 illustrates another modification of a rotating disc according to the present invention having wide apertures to produce long interrupted light-streaks and short intervals between the light-streaks.
Figure 7:
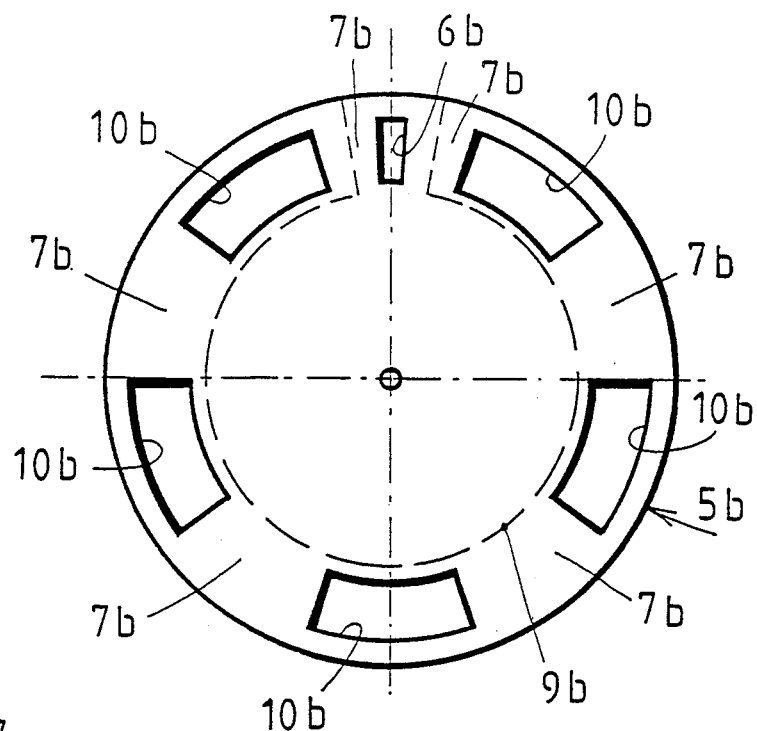
FIG. 7 illustrates a further modification of a rotating disc according to the present invention having wide apertures to produce long interrupted light-streaks and long intervals between the light streaks.

Referring now to FIG. 3, rotating disc 5 has one transparent aperture 6 and a pair of sets of three filter apertures 8 located on either side of the transparent aperture 6. Filter apertures 8 are circumferentially spaced from one another and from transparent aperture 6. Disc 5 is provided with a set of opaque regions 7 between adjacent filter apertures 8 for separating filter apertures 8 from one another and transparent aperture 6 from filter apertures 8. A pair of arcuate filter plates 9 are connected to the disc 5 and are configured to cover the filter apertures 8. Disc 5a, as best seen in FIG. 4, may be used in place of disc 5 in the apparatus of the present invention. Disc 5a is similar to disc 5 and is provided with a pair of two sets of three filter apertures 10 and also a pair of oppositely disposed transparent apertures 6a. Opaque regions 7a of disc 5a separate filter apertures 10 from one another and the transparent apertures 6a from the filter apertures 10. A pair of arcuate filter plates 9a, which may be identical to the filter plates 9, are connected to the disc 5a and cover the filter apertures 10. Disc 5c, illustrated in FIG. 7, is provided with a set of five filter apertures 10b and a single transparent aperture 6b. Opaque regions 7b separate the filter apertures 10b from one another and the transparent aperture 6b from the apertures 10b. A single filter plate 9b is connected to the disc 5b and covers the filter apertures. Any of the discs may be formed from a transparent material which is covered with black plastic. Openings are then defined in the plastic to produce the apertures in the discs 5, 5a and 5b. The filter plates 9, 9a and 9b are connected to their respective discs 5, 5a and 5c with a suitable adhesive.

The discs 5, 5a and 5b may be rotated manually or by motor 2. With reference to FIG. 2, the discs may be manually rotated by manually setting the flywheel 14 in motion. The tachometer 11 registers the rotation speed of the disc. The inertia provided by the rotating disc and the flywheel, together with the bearings 13, ensures a sufficient continuity to the rotation of the discs. Alternatively, as previously discussed, the motor 2 may be used to rotate either of the discs. The motor 2 is powered by a battery 15. Although not illustrated, the rotation speed of the motor, as would be well known in the art, could be controlled by potentiometers forming a component of a suitable electric circuit.

Figure 5:
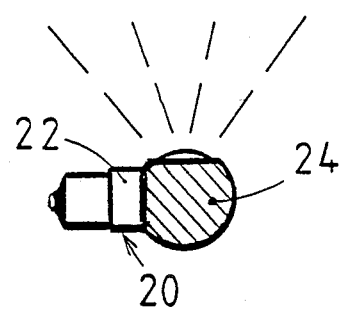
FIG. 5 illustrates a miniature spotlight of the present invention.
Figure 6:
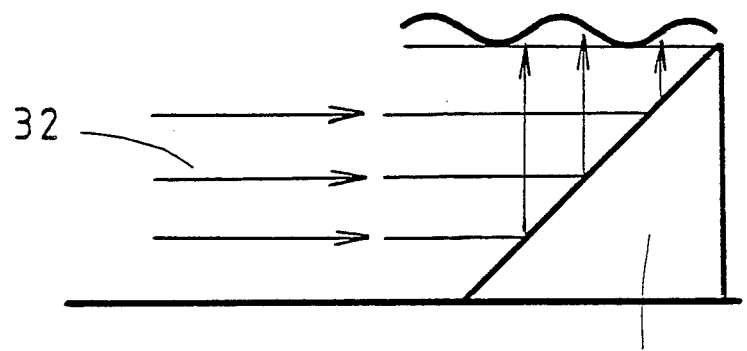
FIG. 6 is a schematic illustration of the employment of the darkened backdrop utilized in the present invention.

The aparatus described above is preferably utilized in conjunction with at least one miniature spotlight illustrated in FIG. 5 and a reflecting darkened backdrop 30 illustrated in FIG. 6. As illustrated in FIG. 5, the miniature spotlight 20 comprises a small incandescent lamp 22 having an aluminum shell-like coating 24. Preferably the lamp 22 is powered by a six-volt, one half amp, electrical power source. Such a power source, which could be a battery, when connected to the lamp 22 provides a sufficient light intensity for purposes of the present invention. With reference to FIG. 6, the darkened reflecting backdrop 30 is set at an angle so that the incident light 32, produced by, for instance, natural sunlight, reflects in an upward direction away from the apparatus of the present invention. The purpose of the backdrop is to eliminate the light reflected from the background and enhance the visibility of the spotlight 20.

The apparatus may be operated in natural lighting conditions provided by the sun with a rotating disc 5 such as illustrated in FIG. 3. Preferably, the spotlight is formed to produce an essentially red light beam. The filter plates 9 are constructed from a red light filtering material that permits the transmission of the red light, emitted by the spot-light 20, through the filter apertures 8. The natural light 32, that is not absorbed and reflected by the darkened back-drop 30, is reflected from the subject. However, the reflected light is of such low intensity that it is fully absorbed by the filter plates 8. As a result, when the disc 5 is made to rotate at a present speed such that the aperture 6 passes the lens of the camera a plurality of times during the exposure time of the film within the camera, the photograph produced by the camera includes a series of images of light-streaks, that are generated from the emitted red light of the miniature spotlights 20 passing through the filter apertures 8. Interruptions between the light-streaks are produced by the opaque regions of the disc located between the filter aparatus. Such a photograph also includes a series of stroboscopic images of the subject from the reflected light passing through the transparent aperture 6 wherein a stroboscopic image is produced each time the transparent aperture 6 passes in front of the camera. Since the subject is moving, a series of stroboscopic images of the subject are produced along with the light-streaks.

If the apertures 10 and 10b of the respective discs 5a and 5b are compared with the apertures 8 of disc 5, the apertures 10 and 10b are wider than the apertures 8 and the apertures 10b are wider than the apertures 8 but narrower than the apertures 10. Moreover, the opaque regions 7a are narrower than the opaque regions 7 and the opaque regions 7b are wider than either of the opaque regions 7a and 7. As a result, the disc 5a is capable of producing long interrupted light-streaks and short intervals between the light-streaks and the disc 5 is capable of producing short interrupted light-streaks with long intervals between the light-streaks. Furthermore, the disc 5b is capable of producing light-streaks that are longer than disc 5, but shorter than disc 5a, with interruptions between light-streaks that are longer than either of the discs 5 or 5a.

As illustrated, all of the discs 5, 5a and 5b, have about the same diameter. Additionally, the sum of the areas of the transparent apertures 6a of the disc 5a is preferably about equal to the area of either of the transparent apertures 6 or 6b of the respective discs 5 and 5b. When disc 5a is made to rotate at a speed of about half the speed of the discs 5 or 5b, all of the discs produce similar stroboscopic sequences of pictures. As can be appreciated, the advantage of this relative sizing of the areas of the transparent apertures and the scaling of rotation speed of the discs allow the discs to be substituted for one another in a single photographic study with the end result that a range of detail may be produced for the moving points of interest.

As can be appreciated, a disc fabricated in accordance with the present invention may have even more than two transparent apertures depending upon the desired photographic effects to be produced. Preferably, again, as a general rule, as between discs of equal diameter, the sum of the areas of the transparent apertures, in a disc having more than one transparent aperture, should be approximately equal to the area of the transparent aperture of a disc having one transparent aperture so that the speed of the discs may be appropeiately scaled to produce similar stroboscopic sequences of pictures and detailed studies of moving points of interest. Furthermore, the number and orientation of the filter apertures may vary as in the discs 5, 5a and 5b. In fact, the number of filter apertures may be selected to equal the number of desired light-streak images as there are filter apertures.

An example of the photographs that can be obtained through the method and apparatus of the present invention appears on pages 14 and 15. The disc used is illustrated in FIG. 7 and the camera was a Canon T-70 with a lens having a focal length of about 50 mm and the aperture was 1.2. The exposure time "t" of one picture in the series of pictures in a photograph is in accordance with the following formula:

$$\frac{1}{t} = \frac{2\pi rn}{d} ;$$

where r is the mean distance of the transparent aperture from the center of the disc, for instance, aperture 6b; n is the rotation speed of the disc; and d is the mean width of the transparent aperture. The speed of the film which is in accordance with the exposure time calculated according to the above formula, prevents each stroboscobic image of the subject from having a blurred appearance in the photograph produced by the camera. Photographs were produced with a disc having an "r" value approximately equal to 20 centimeters, a rotation speed "n" equal to 150 and 240 revolutions per minute and a mean width "d" of the transparent aperture equal to about 2 centimeters. The speed of the film was ISO 400. Such photographs were filed with the application and, because they were in color, do not form part of the application because of lack of reproducibility in the printed patent copy.

Additionally, the transparency of the filter plates 9b was selected such that the incident light from the natural lighting source was visible through the filter plates, when it produced a reading of approximately 8 on an exposure meter, but the light reflected from a shadow was not visible (darkness) through the filter plates when it produced a reading of approximately 5 on the exposure meter. Hand-held batteries connected to the small incandescent lamps, such as illustrated in FIG. 5, were used to produce the light streaks. As illustrated, the subject held the batteries and one lamp. A second lamp was attached to a leg and a third to the middle of the body. The reading on the exposure meter of the incident background light was between about 8 and 10. The reflected light from the backdrop produced exposure meter readings of between about 1 and 3. The reflected light from the subject produced exposure meter readings of between about 5.5 and 7.5. The distance of the camera from the subject was 5 meters. Lastly, the subject wore blue trousers and a green shirt.

The present invention may also be used with artificial background lighting that is preferably produced by a sodium vapor lamp in place of natural lighting. Since the yellow light of the sodium lamp is more efficiently absorbed in the preferred filter plates 9, 9a and 9b the light beams produced by the spotlights may be of less intensity than the light beams that are necessary when using natural lighting. Additionally, the backdrop need not be as dark as compared with the backdrop that is used with natural lighting.

Figure 8:
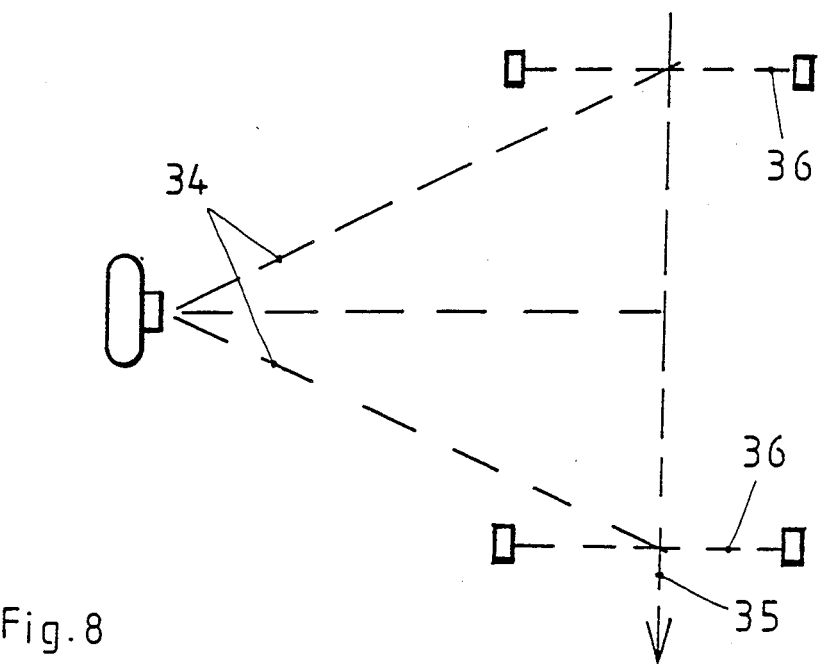
FIG. 8 is a schematic illustration of an automatic infrared ray triggering device that may be connected to the camera.

As illustrated in FIG. 8, in a manner well known in the art, the camera 1 could also be connected to an automatic infrared triggering device 36 set within the viewing field 34 of the camera. An object moving along path would automatically trigger the camera when passing the trigger device 36 and thus, within the viewing field of the camera.

While there has been shown what is considered to be the preferred embodiments of the invention, it will be obvious to those skilled in the art that various changes and modifications may be made therein without departing from the scope of the invention.

I claim:

1. An apparatus for photographing a moving subject in order to study the motion of said subject wherein said subject is externally illuminated by a background lighting source and said subject has means for generating at least one light beam of essentially one selected wavelength from at least one moving point of said subject, said apparatus comprising:
   a camera;
   means for mounting said camera in front of said subject;
   a disc having at least one transparent aperture allowing transmission of the light of said background lighting source reflected from said subject, a plurality of filter apertures circumferentially spaced from one another and from said at least one transparent aperture, a plurality of opaque regions of said disc separating said filter apertures from one another and said at least one transparent aperture from said filter apertures, and means, connected to said disc and associated with filter apertures, for filtering light such that only the light of said essentially one selected wavelength is transmitted through said filter apertures; and
   means, connected to said mounting means, for rotating said disc in front of said camera such that said at least one light beam and said reflected light enter said camera through, respectively, said filter and transparent apertures, whereby a photograph produced by said camera comprises a series of light-streaks produced by said at least one light beam entering said camera through said filter apertures, a series of interruptions between said light-streaks produced by said opaque regions between said filter apertures and a series of stroboscopic images of said subject produced by said reflected light entering said camera through said at leat one transparent aperture.

2. The apparatus of claim 1 wherein said filter apertures comprise a pair of sets of three apertures located on either side of said at least one transparent aperture.

3. The apparatus of claim 2 wherein said disc has a pair of said transparent apertures located opposite to one another and between said sets of filter apertures.

4. The apparatus of claim 1 wherein:
   said disc is fabricated from a transparent material covered with black plastic;
   said filter and said at least one transparent apertures are defined by openings in said black plastic; and
   said filter means comprises an arcuate filter plate configured to cover said filter apertures and to allow transmission of said light of said essentially one selected wavelength.

5. The apparatus of claim 2 wherein:
   said disc is fabricated from a transparent material covered with black plastic;
   said filter and said transparent apertures are defined by openings in said black plastic; and
   said filter means comprises a pair of arcuate filter plates configured to cover said filter apertures and to allow transmission of only said light of said essentially one selected wavelength.

6. The apparatus of claim 3 wherein:
   said disc is fabricated from a transparent material covered with black plastic;
   said filter and said transparent apertures are defined by openings in said black plastic; and
   said filter means comprises a pair of arcuate filter plates configured to cover said filter apertures and to allow transmission of only said light of said essentially one selected wavelength.

7. A method for photographing a moving object in order to study the motion of said subject, comprising:
   providing a background lighting source to illuminate said subject;
   generating at least one light beam of essentially one selected wave length with means connected to at least one moving point;
   providing a darkened backdrop, behind the subject, for eliminating the background light and enhancing the visibility of said at least one light beam;
   photographing the subject by mounting a camera in front of the subject;
   obtaining one selected wavelength from a disc having at least one transparent aperture for transmission, through the disc, of the light of the background lighting source reflected from the subject, the disc having filter apertures and a plurality of opaque regions separating the filter apertures from one another and the at least one transparent aperture from the filter apertures, said lights filtered so that only the light of the essentially one selected wavelength is transmitted through the filter apertures;
   producing a series of interruptions between the light-streaks by the opaque regions between the filter apertures; and
   producing a series of stroboscopic images of the subject by the reflected light entering the camera through the at least one transparent aperture.

8. The method of claim 7, including fabricating the disc from a transparent material covered with black plastic.

9. The method of claim 8, including controlling the rotation of the disc.

10. The method of claim 9, including using a motor to rotate the disc.

11. The method of claim 9, including using a wheel to obtain the rotation speed of the disc.

12. The method of claim 7, including controlling the rotation of the disc.

13. The method of claim 7, including controlling the rotation of the disc by means of a motor.

14. The method of claim 7, including obtaining the rotation speed of the disc from a wheel.

15. The method of claim 7, further including automatically triggering the camera by means of an infrared triggering device located within the viewing field of the camera and along the the path of the subject.

16. The apparatus of claim 1 wherein said camera and said disc are orthogonally related.

* * * * *